US006815571B1

(12) United States Patent
Wittkowski et al.

(10) Patent No.: US 6,815,571 B1
(45) Date of Patent: Nov. 9, 2004

(54) METHOD FOR PRODUCING ETHYLENE POLYMERS IN A HIGH-PRESSURE PROCESS

(75) Inventors: Lars Wittkowski, Mannheim (DE); Andreas Deckers, Flomborn (DE); Wilhelm Weber, Neustadt (DE); Thomas Dröge, Neustadt (DE); Andrei Gonioukh, Liblar (DE); Frank-Olaf Mähling, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/466,117

(22) PCT Filed: Jan. 22, 2002

(86) PCT No.: PCT/EP02/00575

§ 371 (c)(1),
(2), (4) Date: Jul. 23, 2003

(87) PCT Pub. No.: WO02/059166

PCT Pub. Date: Aug. 1, 2002

(30) Foreign Application Priority Data

Jan. 23, 2001 (DE) .......................................... 101 02 937

(51) Int. Cl.$^7$ .............................. C07C 2/02; C08F 2/38
(52) U.S. Cl. ........................... 585/520; 585/9; 585/946; 526/208
(58) Field of Search ................................ 585/520, 946, 585/9; 526/208

(56) References Cited

U.S. PATENT DOCUMENTS

| 3,334,081 A | | 8/1967 | Madgwick et al. | |
| 3,963,690 A | | 6/1976 | Lovett et al. | |
| 4,820,876 A | * | 4/1989 | Nuttens et al. | ................ 585/9 |

FOREIGN PATENT DOCUMENTS

| DE | 1 908 964 | 9/1970 |
| DE | 100 64 799 | 6/2002 |
| DE | 100 64 800 | 6/2002 |
| DE | 100 64 752 | 7/2002 |
| EP | 0 175 316 | 3/1986 |
| EP | 0 449 092 | 10/1991 |
| EP | 0 573 869 | 12/1993 |
| EP | 0 928 797 | 7/1999 |
| WO | WO 02/059166 A1 | 8/2002 |

OTHER PUBLICATIONS

Ullmann's Encyclopaedie Der Techn. Chemie, vol. 24, No. 36, pp. 1–24.
Ullmann's Encyclopaedie Der Techn. Chemie, vol. 19, No. 173, pp. 172–178.

\* cited by examiner

*Primary Examiner*—Fred Teskin
(74) *Attorney, Agent, or Firm*—Oblon, Spivak, McClelland, Maier & Neustadt, P.C.

(57) ABSTRACT

A process for preparing ethylene polymers by the high-pressure method comprises dissolving one or more free-radical initiators in one or more ketones of the formula I

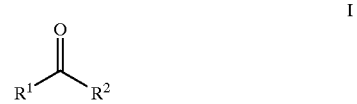

where $R^1$ and $R^2$ are identical or different and are selected from among $C_1$–$C_6$-alkyl and $C_3$–$C_{12}$-cycloalkyl and $R^1$ and $R^2$ may also be covalently linked to one another to form a 4- to 13-membered ring, prior to the polymerization, compressing the solution, metering it into the polymerization reactor at one or more points and subsequently carrying out the polymerization at from 150 to 380° C. and from 500 to 4500 bar.

14 Claims, No Drawings

METHOD FOR PRODUCING ETHYLENE POLYMERS IN A HIGH-PRESSURE PROCESS

The present invention relates to a process for preparing ethylene polymers by the high-pressure method, which comprises dissolving one or more free-radical initiators in one or more ketones of the formula I

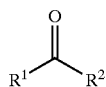

where $R^1$ and $R^2$ are identical or different and are selected from among $C_1$–$C_6$-alkyl and $C_3$–$C_{12}$-cycloalkyl and $R^1$ and $R^2$ may also be covalently linked to one another to form a 4- to 13-membered ring, prior to the polymerization, compressing the solution, metering it into the polymerization reactor at one or more points and subsequently carrying out the polymerization at from 150 to 380° C. and from 500 to 4500 bar.

Ethylene polymers can be prepared by various methods which can be subdivided broadly into low-pressure processes carried out at from 20 to 100 bar and temperatures up to 110° C., and high-pressure processes carried out at from 500 to 4000 bar and temperatures of 150° C. and above. The high-pressure method is a free-radical polymerization process which can generally make do without a catalyst (cf., for example: *Ullmann's Enyclopädie der technischen Chemie*, 4$^{th}$ edition, keywords: waxes, Vol. 24, p. 36 ff., Thieme Verlag Stuttgart, 1977). To initiate the free-radical chain reaction, use is usually made of one or more organic peroxides, for example the Trigonox® or Perkadox® grades from Akzo Nobel, or else air or atmospheric oxygen. The process is generally carried out in high-pressure autoclaves or in tube reactors. High-pressure autoclaves are known in squat or elongated designs. The frequently used tube reactors (*Ullmanns Encyclopädie der technischen Chemie*, Volume 19, p. 169 and p. 173 ff (1980), Verlag Chemie Weinheim, Deerfield Beach, Basle, and *Ullmann's Enyclopädie der technischen Chemie*, 4$^{th}$ edition, keywords: waxes, Vol. 24, p. 36 ff., Thieme Verlag Stuttgart, 1977) are easy to handle and have a low maintenance requirement.

To set the appropriate molecular weight, use is made of substances known as molecular weight regulators or simply regulators. When a substance is used as regulator, it has to be ensured that it is sufficiently efficient because the introduction of very large amounts of regulators is uneconomical.

A frequently used regulator is hydrogen, but when air or atmospheric oxygen is used as free-radical initiator in free-radical polymerization processes it can lead to the formation of explosive hydrogen/oxygen mixtures and is therefore of concern for safety reasons.

Gaseous regulators such as the frequently used alkanes ethane and propane likewise require strict safety regulation.

Ketones are known as particularly advantageous regulators because they are suitable for preparing excellent products having advantageous organoleptic properties, as has been demonstrated, for example, in DE-A 100 64 752, DE-A 100 64 799 and DE-A 100 64 800, published on Jun. 27, 2002. However, the consumption of ketones should be kept as low as possible for cost reasons.

The use of ketones as molecular weight regulators in the preparation of high molecular weight LDPE is likewise known. EP-A 0 928 797 proposes a process using methyl ethyl ketone as regulator, by means of which an LDPE suitable for extruded products, for example for films having a good puncture resistance, are prepared. However, the consumption of regulators is very high, which represents an economic disadvantage. If one wished to prepare waxes by the process described in EP-A 0 928 797, the consumption of regulators would be substantially higher still.

DE-A 1 908 964 discloses a process by means of which ethylene homopolymers can be prepared by the high-pressure method. The process described uses a peroxidic free-radical initiator, advantageously dissolved in an inert solvent (p. 4), in the first reaction zone and air in the second. As regulators, propionaldehyde or methyl ethyl ketone are recommended. In this process, ethylene, free-radical initiator and regulator are metered simultaneously into the first reaction zone of the reactor while air and a further regulator are metered into a second reaction zone. The process described is costly from a logistic and process engineering point of view.

U.S. Pat. No. 3,334,081 describes a high-pressure polymerization process having an increased conversion which is based on feeding ethylene into the reactor at at least two different places. A large number of organic peroxides are recommended as free-radical initiators and a large number of organic compounds, preferably ketones such as methyl ethyl ketone, are recommended as regulators. However, a disadvantage of the process described is the high capital cost resulting from the numerous metering points which all have to be designed so as to be extremely pressure-stable and leak-free. This makes the capital cost of a polymerization plant very high.

It is an object of the present invention to provide a process by means of which polyethylene, for example polyethylene waxes or high molecular weight polyethylene, can be prepared by the high-pressure method and in which both the consumption of process solvents and regulators, in particular of ketones as regulators, and the number and amount of various process chemicals is very low.

We have found that this process is achieved by dissolving one or more free-radical initiators directly in a ketone or a mixture of a plurality of ketones, subsequently compressing the solution and metering it into the polymerization apparatus and then carrying out the polymerization under high-pressure conditions.

Regulators used are one or more aliphatic, cycloaliphatic or alicyclic ketones of the formula I

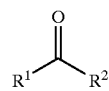

In this formula, the radicals $R^1$ and $R^2$ are identical or different and are selected from among $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl.

In a particular embodiment, the radicals $R^1$ and $R^2$ are covalently joined to one another to form a 4- to 13-membered ring. Thus, for example, $R^1$ and $R^2$ can together be:

—(CH$_2$)$_4$—, —(CH$_2$)$_5$—, —(CH$_2$)$_6$, —(CH$_2$)$_7$—, —CH(CH$_3$)—CH$_2$—CH$_2$—CH(CH$_3$)—
or
—CH(CH$_3$)—CH$_2$—CH$_2$—CH$_2$—CH(CH$_3$)—.

Preferred examples are acetone, methyl ethyl ketone (MEK), methyl isobutyl ketone (MIBK), 2-pentanone, 3-pentanone and cyclopentanone, cyclohexanone and cycloheptanone. Particularly preferred examples are acetone, methyl ethyl ketone, methyl isobutyl ketone and cyclohexanone; very particular preference is given to methyl ethyl ketone and cyclohexanone.

Free-radical initiators used are one or more peroxides selected from among the commercially available substances didecanoyl peroxide, 2,5-dimethyl-2,5-di(2-ethylhexanoylperoxy)hexane, tert-amyl peroxy-2-ethylhexanoate, dibenzoyl peroxide, tert-butyl peroxy-2-ethylhexanoate, tert-butyl peroxydiethylacetate, tert-butyl peroxydiethylisobutyrate, 1,4-di(tert-butylperoxycarbo)cyclohexane as isomer mixture, tert-butyl perisononanoate, 1,1-di(tert-butylperoxy)-3,3,5-trimethylcyclohexane, 1,1-di(tert-butylperoxy)cyclohexane, methyl isobutyl ketone peroxide, tert-butyl peroxyisopropylcarbonate, 2,2-di(tert-butylperoxy)butane or tert-butyl peroxyacetate;

tert-butyl peroxybenzoate, di-tert-amyl peroxide, dicumyl peroxide, the isomeric di(tert-butylperoxyisopropyl)benzenes, 2,5-dimethyl-2,5-di-tert-butylperoxyhexane, tert-butyl cumyl peroxide, 2,5-dimethyl-2,5-di(tert-butylperoxy)hex-3-yne, di-tert-butyl peroxide, 1,3-diisopropyl monohydroperoxide, cumene hydroperoxide or tert-butyl hydroperoxide; or dimeric or trimeric ketone peroxides of the formulae IIa to IIc.

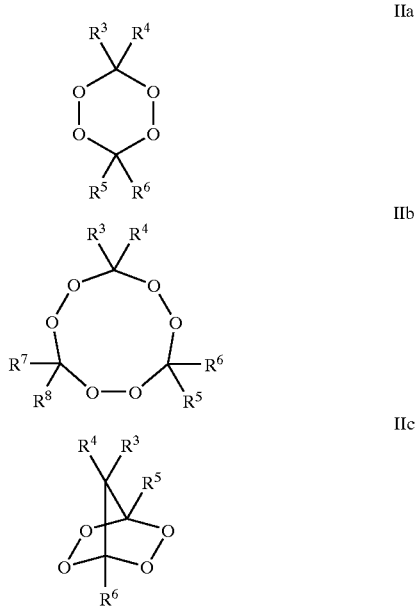

In these formulae, the radicals R$^3$ to R$^8$ are identical or different and are selected from among C$_1$–C$_8$-alkyl such as methyl, ethyl, n-propyl, isopropyl, n-butyl, sec-butyl, isobutyl, tert-butyl, n-pentyl, sec-pentyl, isopentyl, n-hexyl, n-heptyl, n-octyl; preferably linear C$_1$–C6-alkyl such as methyl, ethyl, n-propyl, n-butyl, isobutyl, n-pentyl, isopentyl, n-hexyl, isohexyl, sec-hexyl, particularly preferably linear C$_1$–C$_4$-alkyl such as methyl, ethyl, n-propyl or n-butyl, very particularly preferably ethyl;

C$_6$–C$_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.

Peroxides of the formulae IIa to IIc and processes for preparing them are known from EP-A 0 813 550.

One or more peroxides which can be procured commercially in solid or neat form or in solution are dissolved in one or more ketones of the formula I. Optionally, further customary solvents for stabilizing the free-radical initiators, for example water, toluene, chlorobenzene, white oil, silicone oils or preferably aliphatic solvents such as isododecane, Exxsol® or Isopar Fluids® from Exxon, may be added. However, preference is given to using no further solvents.

Concentrations of the free-radical initiator(s) which have been found to be useful are from 5 to 35% by weight, preferably from 10 to 30% by weight and particularly preferably from 15 to 25% by weight.

If the free-radical initiator is in liquid form at room temperature, dilution of the free-radical initiator with one or more ketones also constitutes an embodiment of the present invention. In this case, it is of no consequence whether the liquid film is present because the initiator has a melting point below room temperature or it is sold commercially only as a highly concentrated, stabilized solution in a hydrocarbon for safety reasons.

The solution of the free-radical initiator or initiators is subsequently compressed in a manner known per se, metered into the polymerization reactor at one or more points and the polymerization is then carried out. Compression is carried out with cooling or preferably at room temperature. Despite the fact that the peroxides used decompose easily, mixing and compression are possible without posing a danger.

It is also possible to store the prepared solutions comprising ketone or ketones, one or more free-radical initiators and optionally the solvent for a relatively long time or, if necessary, to pump them through relatively long pipes without decomposition of the peroxides being observed.

In the process of the present invention, the polymerization or copolymerization is usually carried out at pressures of from 400 to 4500 bar, preferably from 500 to 4000 bar and particularly preferably from 1000 to 3500 bar.

The polymerization temperature is from 140 to 350° C., preferably from 200 to 320° C.

The polyethylenes obtainable by the process described have a density of from 0.900 to 0.955 g/cm$^3$, preferably from 0.910 to 0.945 g/cm$^3$ and particularly preferably from 0.915 to 0.940 g/cm$^3$, measured at 23° C. Polyethylene waxes having a molecular weight M$_w$ of not more than 40,000 g/mol, preferably not more than 10,000 g/mol and particularly preferably not more than 7500 g/mol, can be prepared by the process of the present invention. The molecular weight distribution is in the range from 2 to 10. The melting points are in the range from 60 to 125° C., preferably from 80 to 120° C. However, the process of the present invention is also well suited to preparing relatively high molecular weight LDPE having a molecular weight M$_w$ greater than 40,000 g/mol, preferably greater than 80,000 g/mol and particularly preferably greater than 120,000 g/mol. The molecular weight distribution of the relatively high molecular weight LDPE prepared by the process of the present invention is in the range from 2 to 20. The melting points of the relatively high molecular weight LDPE prepared by the process of the present invention are in the range from 80 to 135° C., preferably from 100 to 125° C.

It is also possible to prepare copolymers of ethylene, in which case all olefins which can be copolymerized with ethylene by a free-radical mechanism are in principle suitable as comonomers. Preference is given to 1-olefins such as propylene, 1-butene, 1-pentene, 1-hexene, 1-octene and 1-decene, acrylates such as acrylic acid, methyl acrylate, ethyl acrylate, n-butyl acrylate, 2-ethylhexyl acrylate or tert-butyl acrylate;

methacrylic acid, methyl methacrylate, ethyl methacrylate, n-butyl methacrylate or tert-butyl methacrylate;

vinyl carboxylates, with vinyl acetate being particularly preferred, unsaturated dicarboxylic acids, particularly preferably maleic acid, unsaturated dicarboxylic acid derivatives, particularly preferably maleic anhydride and alkylimides of maleic acid, for example N-methylmaleimide.

The proportion of comonomer is not more than 50 mol %, preferably not more than 20 mol %.

The process of the present invention allows the polymerization to be carried out with a significant saving of regulators, free-radical initiators and solvents. This means, firstly, a saving of starting materials and, secondly, solvent residues or decomposition products of the free-radical initiator, for example, do not have to be removed from the product after the reaction. Furthermore, the reduced number of starting materials reduces the logistic outlay in production and, in addition, the safety of the process is substantially increased.

In addition, a higher conversion is observed in the process of the present invention than when, as in the prior art, a solution of the free-radical initiator and the regulator are metered in separately.

The polyethylene waxes and relatively high molecular weight ethylene polymers prepared by the process of the present invention display very good organoleptic properties, in particular they are odor neutral and taste neutral. Organoleptic properties can be measured by means of instruments, for example by gas chromatography or by differential thermal analysis, with the amount and type of volatile compounds given off being determined by separate or sequential measuring apparatuses. Tests by a team of test persons are of high significance.

Owing to their very good organoleptic properties, the polymers having a molecular weight of $M_w$ of not more than 40,000 g/mol obtainable by the process of the present invention can be used advantageously for preparations and applications in decorative cosmetics, for example lipsticks, face powders, eyeshadow, eyeliner pencils, foundations, makeup preparations, mascara and eyebrow pencils. The ethylene polymers having a molecular weight $M_w$ above 40,000 g/mol obtainable by the process of the present invention are, for example, very suitable for the production of bags for food packaging.

The polyethylene waxes prepared by the process of the present invention are also very suitable for the preparation of oxidation products.

The invention is illustrated by the examples.

Ethylene was polymerized in a high-pressure autoclave as described in the literature (M. Buback et al., *Chem. Ing. Tech.* 1994, 66, 510).

For each of experiments 1 and 2, a solution of free-radical initiator in methyl ethyl ketone was made up. The rates at which an equimolar mixture of the peroxides tert-butyl peroxypivalate and tert-butyl peroxy-3,3,3-trimethylhexanoate as free radical initiators in methyl ethyl ketone were introduced are shown in Table 1. Subsequently, monomer or monomer mixture was fed in through one line and the solution of free-radical initiators in methyl ethyl ketone was fed in through a second line under the reaction pressure of 1700 bar. The polymerization was carried out at 260° C.

For each of the comparative experiments C1–C3, a mixture of isododecane and the free-radical initiators was made up. The rate at which isododecane and free-radical initiator (mixture of tert-butyl peroxypivalate and tert-butyl peroxy-3,3,3-trimethylhexanoate in a molar ratio of 1.7:1) were introduced are likewise shown in Table 1. Subsequently, monomer or monomer mixture was fed in through one line, the mixture of isododecane and free-radical initiators was fed in through a second line and the regulator methyl ethyl ketone was fed in through a third line under the reaction pressure of 1700 bar. The polymerization was again carried out at 260° C.

TABLE 1

Polymerization conditions in examples 1–2 and comparative examples C1–C3.

| No. | MEK [l/h] | i-$C_{12}$ [l/h] | Ethylene [kg/h] | Peroxide mol/h | PE kg/h | h mm²/s | Conversion % |
|---|---|---|---|---|---|---|---|
| 1 | 1.93 | — | 9.9 | 0.010 | 2.8 | 300 | 28.3 |
| 2 | 1.01 | — | 10.1 | 0.012 | 2.7 | 1720 | 26.7 |
| C1 | 1.17 | 0.64 | 11.8 | 0.013 | 2.8 | 750 | 23.7 |
| C2 | 0.90 | 0.54 | 11.6 | 0.011 | 2.0 | 1500 | 17.2 |
| C3 | 0.75 | 0.57 | 12.0 | 0.011 | 2.5 | 3100 | 20.8 |

Abbreviations used: MEK = methyl ethyl ketone, i-$C_{12}$ = isododecane, PE = polyethylene.

Polymerizations at 220° C.:

For each of experiments 3 and 4, a solution of free-radical initiator in methyl ethyl ketone was made up. The rate at which methyl ethyl ketone and tert-butyl peroxypivalate as free-radical initiator were introduced are shown in Table 2. Subsequently, monomer or monomer mixture was fed in through one line and the solution of tert-butyl peroxypivalate in methyl ethyl ketone was fed in through a second line under the reaction pressure of 1700 bar. The polymerization was carried out at 220° C.

For each of the comparative experiments C4 and C5, a mixture of isododecane and the free-radical initiators was made up. The rates at which isododecane and tert-butyl peroxypivalate as free-radical initiator were introduced are shown in Table 2. Subsequently, monomer or monomer mixture was fed in through one line, the mixture of isododecane and free-radical initiators was fed in through a second line and the regulator methyl ethyl ketone was fed in through a third line under the reaction pressure of 1700 bar. The polymerization was again carried out at 220° C.

TABLE 2

Polymerization conditions in examples 3–4 and comparative examples C4–C5.

| No. | MEK [l/h] | i-$C_{12}$ [l/h] | Ethylene [kg/h] | Peroxide mol/h | PE kg/h | h mm²/s | Conversion % |
|---|---|---|---|---|---|---|---|
| 3 | 1.98 | — | 10.2 | 0.012 | 1.9 | 460 | 18.6 |
| 4 | 1.97 | — | 10.3 | 0.012 | 1.8 | 500 | 17.5 |

TABLE 2-continued

Polymerization conditions in examples 3–4 and comparative examples C4–C5.

| No. | MEK [l/h] | i-$C_{12}$ [l/h] | Ethylene [kg/h] | Peroxide mol/h | PE kg/h | h mm²/s | Conversion % |
|-----|-----------|------------------|-----------------|----------------|---------|---------|--------------|
| C4  | 1.65      | 0.50             | 12.2            | 0.010          | 2.0     | 750     | 16.4         |
| C5  | 2.50      | 0.38             | 10.7            | 0.011          | 1.7     | 200     | 15.9         |

Abbreviations used: MEK = methyl ethyl ketone, i-$C_{12}$ = isododecane, PE = polyethylene.

We claim:

1. A process for preparing a polyethylene wax, comprising:

dissolving one or more free-radical initiators in one or more ketones of the formula I,

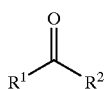

thereby obtaining a solution; and compressing the solution, to obtain a compressed solution;

metering said compressed solution into a polymerization reactor at one or more points; and subsequently polymerizing ethylene, thereby obtaining a polyethylene wax having a molecular weight $M_w$ of not more than 40,000 g/mol;

wherein in formula I, $R^1$ and $R^2$ are identical or different and are $C_1$–$C_6$-alkyl, $C_3$–$C_{12}$-cycloalkyl or $R^1$ and $R^2$ are covalently linked to one another to form a 4- to 13-membered ring, prior to the polymerization;

wherein said process proceeds at a temperature of from 140 to 350° C. and a pressure of from 400 to 4500 bar.

2. The process as claimed in claim 1, wherein the free-radical initiator is dissolved in methyl ethyl ketone.

3. The process as claimed in claim 1, wherein said $C_1$–$C_6$-alkyl is selected from the group consisting of methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, and sec-hexyl.

4. The process as claimed in claim 1, wherein said $C_3$–$C_{12}$-cycloalkyl is selected from the group consisting of cyclopropyl, cyclobutyl, cyclopentyl, cyclohexyl, cycloheptyl, cyclooctyl, cyclononyl, cyclodecyl, cycloundecyl and cyclododecyl.

5. The process as claimed in claim 1, wherein said $R^1$ and $R^2$ are together —$(CH_2)_4$—, —$(CH_2)_5$—, —$(CH_2)_6$—, —$(CH_2)_7$—, —CH($CH_3$)—$CH_2$—$CH_2$—CH($CH_3$)— or —CH($CH_3$)—$CH_2$—$CH_2$—$CH_2$—CH($CH_3$)—.

6. The process as claimed in claim 1, wherein a concentration of the free-radical initiator in said solution is from 5 to 35% by weight.

7. The process as claimed in claim 1, wherein said compression is carried out with cooling.

8. The process as claimed in claim 1, wherein said compression is carried out at room temperature.

9. The process as claimed in claim 1, wherein said polyethylene wax has a density of from 0.900 to 0.955 g/cm³ as measured at 23° C.

10. The process as claimed in claim 1, wherein a molecular weight distribution of said polyethylene wax is in the range from 2 to 10.

11. The process as claimed in claim 1, wherein a melting point of said polyethylene wax is in the range from 60 to 125° C.

12. The process as claimed in claim 1, wherein said ethylene is copolymerized with an olefin.

13. The process as claimed in claim 12, wherein said olefin is added in an amount of from 50 mol %.

14. The process as claimed in claim 1, wherein said ethylene is copolymerized with a comonomer selected from the group consisting of 1-olefins, acrylates, methacrylic acid, methyl methacrylate, ethyl methacrylate, n-butyl methacrylate, tert-butyl methacrylate, vinyl carboxylates, unsaturated dicarboxylic acids, and unsaturated dicarboxylic acid derivatives.

* * * * *